United States Patent [19]

Antos

[11] 4,206,042

[45] Jun. 3, 1980

[54] HYDROCARBON DEHYDROCYCLIZATION WITH AN ACIDIC MULTIMETALLIC CATALYTIC COMPOSITE

[75] Inventor: George J. Antos, Bartlett, Ill.

[73] Assignee: UOP Inc., Des Plaines, Ill.

[21] Appl. No.: 29,508

[22] Filed: Apr. 12, 1979

Related U.S. Application Data

[60] Continuation-in-part of Ser. No. 892,369, Mar. 31, 1978, which is a division of Ser. No. 744,061, Nov. 22, 1976, Pat. No. 4,115,252.

[51] Int. Cl.$^2$ .................. C07C 15/06; C10G 35/08; B01J 23/64
[52] U.S. Cl. ............................ 208/139; 252/441; 252/466 J; 585/407; 585/417; 585/419
[58] Field of Search ............... 585/415, 407, 417, 419; 208/139

[56] References Cited

U.S. PATENT DOCUMENTS

| | | | |
|---|---|---|---|
| 2,662,861 | 12/1953 | Riblett et al. | 208/140 X |
| 2,888,397 | 5/1957 | Burton et al. | 208/138 |
| 2,911,357 | 11/1959 | Myers et al. | 208/139 X |
| 3,759,823 | 9/1973 | Davies et al. | 585/419 X |
| 3,951,782 | 4/1976 | Buss | 208/139 |
| 4,156,640 | 5/1979 | Antos | 208/139 |

*Primary Examiner*—Delbert E. Gantz
*Assistant Examiner*—G. E. Schmitkons
*Attorney, Agent, or Firm*—James R. Hoatson, Jr.; Thomas K. McBride; William H. Page, II

[57] ABSTRACT

Dehydrocyclizable hydrocarbons are converted to aromatics by contacting them at hydrocarbon dehydrocyclization conditions with an acidic multimetallic catalytic composite comprising a combination of catalytically effective amounts of a platinum group component, a cobalt component, a zinc component, and a halogen component with a porous carrier material. The platinum group, cobalt, zinc and halogen components are present in the multimetallic catalyst in amounts respectively, calculated on an elemental basis, corresponding to about 0.01 to about 2 wt. % platinum group metal, about 0.05 to about 5 wt. % cobalt, about 0.01 to about 5 wt. % zinc, and about 0.1 to about 3.5 wt. % halogen. Moreover, the catalytically active sites induced by these metallic components are uniformly dispersed throughout the porous carrier material and these metallic components are present in the catalyst in carefully controlled oxidation states such that substantially all of the platinum group component is in the elemental metallic state, substantially all of the zinc component is preferably in an oxidation state above that of the elemental metal, and substantially all of the catalytically available cobalt component is present in the elemental metallic state or in a state which is reducible to the elemental metallic state under hydrocarbon dehydrocyclization conditions, or in a mixture of these states. A specific example of dehydrocyclization method disclosed herein is a method for converting a feed mixture of n-hexane and n-heptane to a product mixture of benzene and toluene which involves contacting the feed mixture and a hydrogen stream with the acidic multimetallic catalyst disclosed herein at hydrocarbon dehydrocyclization conditions.

27 Claims, No Drawings

HYDROCARBON DEHYDROCYCLIZATION WITH AN ACIDIC MULTIMETALLIC CATALYTIC COMPOSITE

CROSS-REFERENCE TO RELATED APPLICATIONS

This application is a continuation-in-part of my prior, copending application Ser. No. 892,369 filed Mar. 31, 1978, which in turn is a division of my prior application Ser. No. 744,061 filed Nov. 22, 1976 and issued on Sept. 19, 1978 as U.S. Pat. No. 4,115,252. All of the teachings of these prior applications are specifically incorporated herein by reference.

The subject of the present invention is, broadly, an improved method for dehydrocyclizing a dehydrocyclizable hydrocarbon to produce an aromatic hydrocarbon. In a narrower aspect, the present invention involves a method of dehydrocyclizing aliphatic hydrocarbons containing 6 to 20 carbon atoms per molecule to monocyclic aromatic hydrocarbons with minimum production of side products such as $C_1$ to $C_5$ hydrocarbons, bicyclic aromatics, olefins and coke. In another aspect, the present invention relates to the dehydrocyclization use of an acidic multimetallic catalytic composite comprising a combination of catalytically effective amounts of a platinum group component, a cobalt component, a zinc component, and a halogen component with a porous carrier material. This acidic multimetallic composite has been found to possess highly beneficial characteristics of activity, selectivity, and stability when it is employed in the dehydrocyclization of dehydrocyclizable hydrocarbons to make aromatics such as benzene, toluene and xylene.

The conception of the present invention followed from my search for a novel catalytic composite possessing a hydrogenation-dehydrogenation function, a controllable cracking and isomerization function, and superior conversion, selectivity, and stability characteristics when employed in hydrocarbon conversion processes that have traditionally utilized dual-function catalytic composites. In my prior applications, I disclosed a significant finding with respect to a multimetallic catalytic composite meeting these requirements. More specifically, I determined that a combination of specified amounts of a cobalt component and a zinc component can be utilized, under certain conditions, to beneficially interact with the platinum group component of a dual-function acidic catalyst with a resultant marked improvement in the performance of such a catalyst. Now I have ascertained that an acidic multimetallic catalytic composite, comprising a combination of catalytically effective amounts of a platinum group component, a cobalt component, a zinc component and a halogen component with a porous carrier material, can have superior activity, selectivity, and stability characteristics when it is employed in a ring-closure or dehydrocyclization process if the catalytically active sites induced by these components are uniformly dispersed in the porous carrier material in the amounts specified hereinafter and if the oxidation state of the active metallic ingredients are carefully controlled so that substantially all of the platinum group component is present in the elemental metallic state, substantially all of the zinc component is preferably present in a positive oxidation state, and substantially all of the catalytically available cobalt component is present in the elemental metallic state or in a state which is reducible to the elemental metallic state under hydrocarbon dehydrocylization conditions or in a mixture of these states.

The dehydrocyclization of dehydrocyclizable hydrocarbons is an important commercial process because of the great and expanding demand for aromatic hydrocarbons for use in the manufacture of various chemical products such as synthetic fibers, insecticides, adhesives, detergents, plastics, synthetic rubbers, pharmaceutical products, high octane gasoline, perfumes, drying oils, ion-exchange resins, and various other products well known to those skilled in the art. One example of this demand is in the manufacture of alkylated aromatics such as ethylbenzene, cumene and dodecylbenzene by using the appropriate mono-olefins to alkylate benzene. Another example of this demand is in the area of chlorination of benzene to give chlorobenzene which is then used to prepare phenol by hydrolysis with sodium hydroxide. The chief use for phenol is of course in the manufacture of phenol-formaldehyde resins and plastics. Another route to phenol uses cumene as a starting material and involves the oxidation of cumene by air to cumene hydroperoxide which can then be decomposed to phenol and acetone by the action of an appropriate acid. The demand for ethylbenzene is primarily derived from its use to manufacture styrene for selective dehydrogenation; styrene is in turn used to make styrene-butadiene rubber and polystyrene. Ortho-xylene is typically oxidized to phthalic anhydride by reaction in vapor phase with air in the presence of a vanadium pentoxide catalyst. Phthalic anhydride is in turn used for production of plasticizers, polyesters and resins. The demand for para-xylene is caused primarily by its use in the manufacture of terephthalic acid or dimethyl terephthalate which in turn is reacted with ethylene glycol and polymerized to yield polyester fibers. Substantial demand for benzene also is associated with its use to produce aniline, Nylon, maleic anhydride, solvents and the like petrochemical products. Toluene, on the other hand, is not, at least relative to benzene and the $C_8$ aromatics, in great demand in the petrochemical industry as a basic building block chemical; consequently, substantial quantities of toluene are hydrodealkylated to benzene or disproportionated to benzene and xylene. Another use for toluene is associated with the transalkylation of trimethylbenzene with toluene to yield xylene.

Responsive to this demand for these aromatic products, the art has developed a number of alternative methods to produce them in commercial quantities. One method that has been widely studied involves the selective dehydrocyclization of a dehydrocyclizable hydrocarbon by contacting the hydrocarbon with a suitable catalyst at dehydrocyclization conditions. As is the case with most catalytic procedures, the principal measure of effectiveness for this dehydrocyclization method involves the ability to perform its intended function with minimum interference of side reactions for extended periods of time. The analytical terms used in the art to broadly measure how well a particular catalyst performs its intended functions in a particular hydrocarbon conversion reaction are activity, selectivity, and stability, and for purposes of discussion here, these terms are generally defined for a given reactant as follows: (1) activity is a measure of the catalyst's ability to convert the hydrocarbon reactant into products at a specified severity level where severity level means the specific reaction conditions used—that is, the temperature, pressure, contact time, and presence of diluents such as $H_2$; (2) selectivity usually refers to the amount of desired product or products obtained relative to the amount of the reactant charged or converted; (3) stability refers to the rate of change with time of the activity and selectivity parameters—obviously the smaller rate implying the more stable catalyst. More specifically, in a dehydrocyclization process, activity commonly refers to the amount of conversion that takes place for a given dehydrocyclizable hydrocarbon at a specified severity level and is typically measured on the basis of disappearance of the dehydrocyclizable hydrocarbon; selectivity is typically measured by the amount, calculated on a weight percent of feed basis or on a mole percent of converted dehydrocyclizable hydrocarbon basis, of the desired aromatic hydrocarbon or hydrocarbons obtained at the particular activity or severity level; and stability is typically equated to the rate of change with time of activity as measured by disappearance of the dehydrocyclizable hydrocarbon and of selectivity as measured by the amount of desired aromatic hydrocarbon produced. Accordingly, the major problem facing workers in the hydrocarbon dehydrocyclization or ring-closure art is the development of a more active and selective catalytic composite that has good stability characteristics.

I have now found a dual-function acidic multimetallic catalytic composite which possesses improved activity, selectivity, and stability when it is employed in a process for the dehydrocyclization of dehydrocyclizable hydrocarbons. In particular, I have determined that the use of an acidic multimetallic catalyst, comprising a combination of catalytically effective amounts of a platinum group component, a cobalt component, a zinc component, and a halogen component with a porous refractory carrier material, can enable the performance of a hydrocarbon dehydrocyclization process to be substantially improved if the catalytically active sites induced by the metallic components are uniformly dispersed throughout the carrier material in the amounts and relative relationships specified hereinafter and if their oxidation states of the active metallic ingredients are carefully controlled to be in the states hereinafter stated. Moreover, particularly good results are obtained when this catalyst is prepared and maintained, during use in the dehydrocyclization method, in a substantially sulfur-free state. This acidic multimetallic catalytic composite is particularly useful in the dehydrocyclization of $C_6$ to $C_{10}$ paraffins to produce aromatic hydrocarbons such as benzene, toluene, and the xylenes with minimization of by-products such as $C_1$ to $C_5$ saturated hydrocarbons, bicyclic aromatics, olefins and coke.

In sum, the current invention involves the significant finding that a combination of a cobalt component and a zinc component can be utilized under the circumstances specified herein to beneficially interact with and promote an acidic dehydrocyclization catalyst containing a platinum group metal when it is used in the production of aromatics by ring-closure of aliphatic hydrocarbons.

It is, accordingly, one object of the present invention to provide a novel method for the dehydrocyclization of dehydrocylizable hydrocarbons utilizing an acidic multimetallic catalytic composite comprising catalytically effective amounts of a platinum group component, a cobalt component, a zinc component and a halogen component combined with a porous carrier material. A second object is to provide a novel acidic catalytic composite having superior performance characteristics when utilized in a dehydrocyclization process. Another object is to provide an improved method for the dehydrocyclization of paraffin hydrocarbons to produce aromatic hydrocarbons which method minimizes undesirable by-products such as $C_1$ to $C_5$ saturated hydrocarbons, bicyclic aromatics, olefins and coke.

In brief summary, one embodiment of the present invention involves a method for dehydrocyclizing a dehydrocyclizable hydrocarbon which comprises contacting the hydrocarbon at hydrocarbon dehydrocyclization conditions with an acidic multimetallic catalytic composite comprising a porous carrier material containing a uniform dispersion of catalytically effective amounts of a platinum group component, a cobalt component, a zinc component, and a halogen component. Moreover, substantially all of the platinum group component is present in the composite in the elemental metallic state, substantially all of the zinc component is preferably present in a positive oxidation state, and substantially all of the catalytically available cobalt component is present in the elemental metallic state or in a state which is reducible to the elemental metallic state under hydrocarbon dehydrocyclization conditions or in a mixture of these states. Further these components are present in this composite in amounts, calculated on an elemental basis, sufficient to result in the composite containing about 0.01 to about 2 wt. % platinum group metal, about 0.05 to about 5 wt. % cobalt, about 0.01 to about 5 wt. % zinc and about 0.1 to about 3.5 wt. % halogen.

A second embodiment relates to the dehydrocyclization method described in the first embodiment wherein the dehydrocyclizable hydrocarbon is an aliphatic hydrocarbon containing 6 to 20 carbon atoms per molecule.

A highly preferred embodiment comprehends the dehydrocyclization method characterized in the first embodiment wherein the catalyst is prepared and maintained in a sulfur-free state and wherein the contacting is performed in a substantially sulfur-free environment.

Another embodiment relates to the catalytic composite used in the first, second or third embodiments and involves the further limitation that the halogen component is chlorine.

Other objects and embodiments of the present invention involve specific details regarding essential and preferred catalytic ingredients, preferred amounts of ingredients, suitable methods of multimetallic composite preparation, suitable dehydrocyclizable hydrocarbons, operating conditions for use in the dehydrocyclization process, and the like particulars. These are hereinafter given in the following detailed discussion of each of these facets of the present invention.

Regarding the dehydrocyclizable hydrocarbon that is subjected to the method of the present invention, it can in general be any aliphatic hydrocarbon or substituted aliphatic hydrocarbon capable of undergoing ring-closure to produce an aromatic hydrocarbon. That is, it is intended to include within the scope of the present invention, the dehydrocyclization of any organic compound capable of undergoing ring-closure to produce an aromatic hydrocarbon containing the same, or less than the same, number of carbon atoms that the reactant compound and capable of being vaporized at the dehydrocyclization temperatures used herein. More particularly, suitable dehydrocyclizable hydrocarbons are: aliphatic hydrocarbons containing 6 to 20 carbon atoms per molecule such as $C_6$ to $C_{20}$ paraffins, $C_6$ to $C_{20}$ olefins and $C_6$ to $C_{20}$ polyolefins. Specific examples of suitable dehydrocyclizable hydrocarbons are: (1) paraffins such as n-hexane, 2-methylpentane, 3-methylpentane, 2,2-dimethylbutane, n-heptane, 2-methylhexane, 3-ethylpentane, 2,2-dimethylpentane, n-octane, 2-methylheptane, 3-ethylhexane, 2,2-dimethylhexane, 2-methyl-3-ethylpentane, 2,2,3-trimethylpentane, n-nonane, 2-methyloctane, 2,2-dimethylheptane, n-decane and the like compounds; (2) olefins such as 1-hexene, 2-methyl-1-pentene, 1-heptene, 1-octene, 1-nonene and the like compounds; and, (3) diolefins such as 1,5-hexadiene, 2-methyl-2,4-hexadiene, 2,6-octadiene and the like diolefins.

In a preferred embodiment, the dehydrocyclizable hydrocarbon is a paraffin hydrocarbon having about 6 to 10 carbon atoms per molecule. For example, paraffin hydrocarbons containing about 6 to 8 carbon atoms per molecule are dehydrocyclized by the subject method to produce the corresponding aromatic hydrocarbon. It is to be understood that the specific dehydrocyclizable hydrocarbons mentioned above can be charged to the present method individually, in admixture with one or more of the other dehydrocyclizable hydrocarbons, or in admixture with other hydrocarbons such as naphthenes, aromatics, $C_1$ to $C_5$ paraffins and the like. Thus mixed hydrocarbon fractions, containing significant quantities of dehydrocyclizable hydrocarbons that are commonly available in a typical refinery, are suitable charge stocks for the instant method; for example, highly paraffinic straight run naphthas, paraffinic raffinates from aromatic extraction or adsorption, $C_6$ to $C_9$ paraffin-rich streams and the like refinery streams. An especially preferred embodiment involves a charge stock which is a paraffin-rich naphtha fraction boiling in the range of about 140° to about 400° F. Generally, best results are obtained with a charge stock comprising a mixture of $C_6$ to $C_9$ paraffins, and especially $C_6$ to $C_9$ normal paraffins.

The acidic multimetallic catalyst used in the present dehydrocyclization method comprises a porous carrier material having combined therewith catalytically effective amounts of a platinum group component, a cobalt component, a zinc component, and a halogen component.

Considering first the porous carrier material utilized in the present invention, it is preferred that the material be a porous, adsorptive, high-surface area support having a surface area of about 25 to about 500 $m^2/g$. The porous carrier material should be relatively refractory to the conditions utilized in the hydrocarbon conversion process, and it is intended to include within the scope of the present invention carrier materials which have traditionally been utilized in dual-function hydrocarbon conversion catalysts such as: (1) activated carbon, coke, or charcoal; (2) silica or silica gel, silicon carbide, clays, and silicates including those synthetically prepared and naturally occurring, which may or may not be acid treated for example, attapulgus clay, china clay, diatomaceous earth, fuller's earth, kaolin, kieselguhr, etc.; (3) ceramics, porcelain, crushed firebrick, bauxite; (4) refractory inorganic oxides such as alumina, titanium dioxide, zirconium dioxide, chromium oxide, beryllium oxide, vanadium oxide, cesium oxide, hafnium oxide, zinc oxide, magnesia, boria, thoria, silica-alumina, silica-magnesia, chromia-alumina, alumina-boria, silica-zirconia, etc.; (5) crystalline zeolitic alumino-silicates such as naturally occurring or synthetically prepared mordenite and/or faujasite, either in the hydrogen form or in a form which has been treated with multivalent cations; (6) spinels such as $MgAl_2O_4$, $FeAl_2O_4$, $ZnAl_2O_4$, $MnAl_2O_4$, $CaAl_2O_4$, and other like compounds having the formula $MO-Al_2O_3$ where M is a metal having a valence of 2; and (7) combinations of elements from one or more of these groups. The preferred porous carrier materials for use in the present invention are refractory inorganic oxides, with best results obtained with an alumina carrier material. Suitable alumina materials are the crystalline aluminas known as gamma-, eta, and theta-alumina, with gamma- or eta-alumina giving best results. In addition, in some embodiments the alumina carrier material may contain minor proportions of other well known refractory inorganic oxides such as silica, zirconia, magnesia, etc.; however, the preferred support is substantially pure gamma- or eta-alumina. Preferred carrier materials have an apparent bulk density of about 0.3 to about 0.8 g/cc and surface area characteristics such that the average pore diameter is about 20 to 300 Angstroms, the pore volume (B.E.T.) is about 0.1 to about 1 cc/g and the surface area (B.E.T.) is about 100 to about 500 $m^2/g$. In general, best results are typically obtained with a gamma-alumina carrier material which is used in the form of spherical particles having: a relatively small diameter (i.e. typically about 1/16 inch), an apparent bulk density of about 0.3 to about 0.8 g/cc, a pore volume (B.E.T.) of about 0.4 cc/g, and a surface area (B.E.T.) of about 100 to about 250 $m^2/g$.

The preferred alumina carrier material may be prepared in any suitable manner and may be synthetically prepared or natural occurring. Whatever type of alumina is employed, it may be activated prior to use by one or more treatments including drying, calcination, steaming, etc., and it may be in a form known as activated alumina, activated alumina of commerce, porous alumina, alumina gel, etc. For example, the alumina carrier may be prepared by adding a suitable alkaline reagent, such as ammonium hydroxide, to a salt of aluminum such as aluminum chloride, aluminum nitrate, etc., in an amount to form an aluminum hydroxide gel which upon drying and calcining is converted to alumina. The alumina carrier may be formed in any desired shape such as spheres, pills, cakes, extrudates, powders, granules, tablets, etc., and utilized in any desired size. For the purpose of the present invention a particularly preferred form of alumina is the sphere, and alumina spheres may be continuously manufactured by the well-known oil drop method which comprises: forming an alumina hydrosol by any of the techniques taught in the art and preferably by reacting aluminum metal with hydrochloric acid, combining the resultant hydrosol with a suitable gelling agent and dropping the resultant mixture into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 300° F. to about 400° F. and subjected to a calcination procedure at a temperature of about 850° F. to about 1300° F. for a period of about 1 to about 20 hours. This treatment effects conversion of the alumina hydrogel to the corresponding crystalline gamma-alumina. See the teachings of U.S. Pat. No. 2,620,314 for additional details.

The expression "catalytically available cobalt" as used herein is intended to mean the portion of the cobalt component of the subject catalytic composite that is available for use in accelerating the dehydrocyclization reaction of interest. For purposes of the present invention, it is highly preferred that the catalytically available cobalt comprise at least about 10% of the total cobalt content of the catalyst and, even more preferably, at least about 50% thereof. For certain types of carrier materials which can be used in the preparation of the instant catalyst composite, it has been observed that a portion of the cobalt incorporated therein is essentially bound-up in the crystal structure thereof in a manner which essentially makes it catalytically unavailable; in fact, it is more a part of the refractory carrier material than a catalytically active component. Specific examples of this effect are observed when the carrier material can form a refractory spinel or spinel-like structure with a portion of the cobalt component and/or when a refractory cobalt oxide or aluminate is formed by reaction of the carrier material (or precursors thereof) with a portion of the cobalt component. When this effect occurs, it is only with great difficulty that the portion of the cobalt bound-up with the support can be reduced to a catalytically active state and the conditions required to do this are beyond the severity levels normally associated with hydrocarbon conversion conditions and are in fact likely to seriously damage the necessary porous characteristics of the support. In the cases where cobalt can interact with the crystal structure of the support to render a portion thereof catalytically unavailable, the concept of the present invention merely requires that the amount of cobalt added to the subject catalyst be adjusted to satisfy the requirements of the support as well as the catalytically available cobalt requirements of the present invention. Against this background then, the hereinafter stated specifications for oxidation state and dispersion of the cobalt component are to be interpreted as directed to a description of the catalytically available cobalt. On the other hand, the specifications for the amount of cobalt used are to be interpreted to include all of the cobalt contained in the catalyst in any form.

One essential constituent of the acidic multimetallic catalyst of the present invention is a zinc component. This component may in general be present in the instant catalytic composite in any catalytically available form such as the elemental metal, a compound like the oxide, hydroxide, halide, oxyhalide, aluminate, or in chemical combination with one or more of the other ingredients of the catalyst. Although it is not intended to restrict the present invention by this explanation it is believed that best results are obtained when the zinc component is present in the composite in a form wherein substantially all of the zinc moiety is in an oxidation state above that of the elemental metal such as in the form of zinc oxide or zinc aluminate, or a mixture thereof, and the subsequently described oxidation and reduction steps that are preferably used in the preparation of the instant catalytic composite are specifically designed to achieve this end. The term "zinc aluminate" as used herein refers to a coordinated complex of zinc, oxygen, and aluminum which are not necessarily present in the same relationship for all cases covered herein. This zinc component can be used in any amount which is catalytically effective, with good results obtained, on an elemental basis, with about 0.01 to about 5 wt. % zinc in the catalyst. Best results are ordinarily achieved with about 0.05 to about 1 wt. % zinc, calculated on an elemental basis.

This zinc component may be incorporated into the catalytic composite in any suitable manner known to the art to result in a relatively uniform dispersion of the zinc moiety in the carrier material, such as by coprecipitation or cogellation with the porous carrier material, ion exchange with the gelled carrier material, or impregnation with the carrier material either after, before, or during the period when it is dried and calcined. It is to be noted that it is intended to include within the scope of the present invention all conventional methods for incorporating and simultaneously uniformly distributing a metallic component in a catalytic composite and the particular method of incorporation used is not deemed to be an essential feature of the present invention. One especially preferred method of incorporating the zinc component into the catalytic composite involves cogelling or coprecipitating the zinc component in the form of the corresponding hydrous oxide during the preparation of the preferred carrier material, alumina. This method typically involves the addition of a suitable sol-soluble zinc compound such as zinc chloride, zinc nitrate, and the like to the alumina hydrosol and then combining the hydrosol with a suitable gelling agent and dropping the resulting mixture into an oil bath, etc., as explained in detail hereinbefore. Alternatively, the zinc compound can be added to the gelling agent. After drying and calcining the resulting gelled carrier material in air, there is obtained an intimate combination of alumina and zinc oxide and/or aluminate. Another preferred method of incorporating the zinc component into the catalytic composite involes utilization of a soluble, decomposable compound of zinc to impregnate the porous carrier material. In general, the solvent used in this impregnation step is selected on the basis of the capability to dissolve the desired zinc compound without adversely affecting the carrier material or the other ingredients of the catalyst—for example, a suitable alcohol, ether, acid and the like solvents. The solvent is preferably an aqueous, acidic solution. Thus, the zinc component may be added to the carrier material by commingling the latter with an aqueous acidic solution of suitable zinc salt, complex, or compound such as zinc acetate, ammonium tetrachlorozincate, zinc borate, zinc bromade, zinc bromide, zinc carbonate, zinc perchlorate, zinc chloride, zinc chloroplatinate, zinc fluoride, zinc formate, zinc hydroxide, zinc nitrate, zinc oxide, any of the soluble zincate salts, and the like compounds. A particularly preferred impregnation solution comprises an acidic aqueous solution of zinc chloride or zinc nitrate. Suitable acids for use in the impregnation solution are: inorganic acids such as hydrochloric acid, nitric acid, and the like, and strongly acidic organic acids such as oxalic acid, malonic acid, citric acid, and the like. In general, the zinc component can be impregnated either prior to, simultaneously with, or after the other ingredients are added to the carrier material, However, excellent results are obtained when the zinc component is added to the carrier material prior to or simultaneously with the addition of the platinum group and cobalt components.

A second essential ingredient of the subject catalyst is the platinum group component. That is, it is intended to cover the use of platinum, iridium, osmium, ruthenium, rhodium, palladium, or mixtures thereof, as a second component of the present composite. It is an essential feature of the present invention that substantially all of this platinum group component exists within the final catalytic composite in the elemental metallic state. Generally, the amount of this component present in the final catalytic composite is small compared to the quantities of the other components combined therewith. In fact, the platinum group component generally will comprise about 0.01 to about 2 wt. % of the final catalytic composite, calculated on an elemental basis. Excellent results are obtained when the catalyst contains about 0.05 to about 1 wt. % of platinum, iridium, rhodium, or palladium metal. Particularly preferred mixtures of these metals are platinum and iridium, and platinum and rhodium.

This platinum group component may be incorporated in the catalytic composite in any suitable manner known to result in a relatively uniform distribution of this component in the carrier material such as coprecipitation or cogelation, ion exchange or impregnation. The preferred method of preparing the catalyst involves the utilization of a soluble, decomposable compound of platinum group metal to impregnate the carrier material in a relatively uniform manner. For example, this component may be added to the support by commingling the latter with an aqueous solution of chloroplatinic or chloroiridic or chloropalladic acid. Other watersoluble compounds or complexes of platinum group metals may be employed in impregnation solutions and include ammonium chloroplatinate, bromoplatinic acid, platinum trichloride, platinum tetrachloride hydrate, platinum dichlorocarbonyl dichloride, dinitrodiaminoplatinum, sodium tetranitroplatinate (II), palladium chloride, palladium nitrate, palladium sulfate, diamminepalladium (II) hydroxide, tetramminepalladium (II) chloride, hexamminerhodium chloride, rhodium carbonylchloride, rhodium trichloride hydrate, rhodium nitrate, sodium hexachlororhodate (III), sodium hexanitrorhodate (III), iridium tribromide, iridium dichloride, iridium tetrachloride, sodium hexanitroiridate (III), potassium or sodium chloroiridate, potassium rhodium oxalate, etc. The utilization of a platinum, iridium, rhodium, or palladium chloride compound, such as chloroplatinic, chloroiridic, or chloropalladic acid or rhodium trichloride hydrate, is preferred since it facilitates the incorporation of both the platinum group components and at least a minor quantity of the halogen component in a single step. Hydrogen chloride or the like acid is also generally added to the impregnation solution in order to further facilitate the incorporation of the halogen component and the uniform distribution of the metallic components throughout the carrier material. In addition, it is generally preferred to impregnate the carrier material after it has been calcined in order to minimize the risk of washing away the valuable platinum or palladium compounds; however, in some cases it may be advantageous to impregnate the carrier material when it is in a gelled state.

A third essential ingredient of the acidic multimetallic catalytic composite used in the present invention is a cobalt component. Although this component may be initially incorporated into the composite in many different decomposable forms which are hereinafter stated, my basic finding is that the catalytically active state for hydrocarbon conversion with this component is the elemental metallic state. Consequently, it is a feature of this invention that substantially all of the catalytically available cobalt component exists in the catalytic composite either in the elemental metallic state or in a state which is reducible to the elemental state under hydrocarbon dehydrocyclization conditions or in a mixture of these states. Examples of this last state are obtained when the catalytically available cobalt component is initially present in the form of cobalt oxide, hydroxide, halide, oxyhalide, and the like reducible compounds. As a corollary to this basic finding on the active state of the catalytically availabe cobalt component, it follows that the presence of the catalytically available cobalt in forms which are not reducible at hydrocarbon dehydrocyclization conditions is to be scrupulously avoided if the full benefits of the present invention are to be realized. Illustrative of these undesired forms are cobalt sulfide and the cobalt oxysulfur compounds such as cobalt sulfate. Best results are obtained when the composite initially contains all of the catalytically available cobalt component in the elemental metallic state or in a reducible oxide state or in a mixture of these states. All available evidence indicates that the preferred preparation procedure specifically described in Example I results in a catalyst having the catalytically available cobalt component in the elemental metal form and/or in a reducible oxide form. Based on the performance of such a catalyst, it is believed that substantially all of this reducible oxide form of the cobalt component is reduced to the elemental metallic state when a dehydrocyclization process using this catalyst is started-up and lined-out at hydrocarbon dehydrocyclization conditions. The cobalt component may be utilized in the composite in any amount which is catalytically effective, with the preferred amount being about 0.05 to about 5 wt. % thereof, calculated on an elemental cobalt basis. Typically, best results are obtained with about 0.1 to about 2.5 wt. % cobalt. It is, additionally, preferred to select the specific amount of cobalt from within this broad weight range as a function of the amount of the platinum group component, on an atomic basis, as is explained hereinafter.

The cobalt component may be incorporated into the catalytic composite in any suitable manner known to those skilled in the catalyst formulation art to result in a relatively uniform distribution of the catalytically available cobalt in the carrier material such as coprecipitation, cogelation, ion exchange, impregnation, etc. In addition, it may be added at any stage of the preparation of the composite—either during preparation of the carrier material or thereafter—since the precise method of incorporation used is not deemed to be critical. However, best results are obtained when the catalytically available cobalt component is relatively uniformly distributed throughout the carrier material in a relatively small particle or crystallite size having a maximum dimension of less than 100 Angstroms, and the preferred procedures are the ones that are known to result in a composite having a relatively uniform distribution of the catalytically available cobalt moiety in a relatively small particle size. One acceptable procedure for incorporating this component into the composite involves cogelling or coprecipitating the cobalt component during the preparation of the preferred carrier material, alumina. This procedure usually comprehends the addition of a soluble, decomposable, and reducible compound of cobalt such as cobalt chloride, acetate or nitrate to the alumina hydrosol before it is gelled. Alternatively, the reducible compound of cobalt can be added to the gelling agent before it is added to the hydrosol. The resulting mixture is then finished by conventional gelling, aging, drying, and calcination steps as explained hereinbefore. One preferred way of incorporating this component is an impregnation step wherein the porous carrier material is impregnated with a suitable cobalt-containing solution either before, during, or after the carrier material is calcined or oxidized. The solvent used to form the impregnation solution may be water, alcohol, ether, or any other suitable organic or inorganic solvent provided the solvent does not adversely interact with any of the other ingredients of the composite or interfere with the distribution and reduction of the cobalt component. Preferred impregnation solutions are aqueous solutions of water-soluble, decomposable, and reducible cobalt compounds such as cobaltous acetate, cobaltous benzoate, cobaltous bromate, cobaltous bromide, cobaltous chlorate and perchlorate, cobaltous chloride, cobaltic chloride, cobaltous fluoride, cobaltous iodide, cobaltous nitrate, hexamminecobalt (III) chloride, hexamminecobalt (III) nitrate, triethylenediamminecobalt (III) chloride, cobaltous hexamethylenetetramine, and the like compounds. Best results are ordinarily obtained when the impregnation solution is an aqueous solution of cobalt chloride or acetate or nitrate. This cobalt component can be added to the carrier material, either prior to, simultaneously with, or after the other metallic components are combined therewith. Best results are usually achieved when this component is added to the porous carrier material simultaneously with the platinum group and zinc components via an acidic aqueous impregnation solution. In fact, excellent results are obtained, as reported in the examples, with an impregnation procedure using an acidic aqueous solution comprising chloroplatinic acid, cobaltous chloride, zinc chloride, and hydrochloric acid to impregnate a porous alumina carrier material.

It is essential to incorporate a halogen component into the acidic multimetallic catalytic composite used in the present invention. Although the precise form of the chemistry of the association of the halogen component with the carrier material is not entirely known, it is customary in the art to refer to the halogen component as being combined with the carrier material, or with the other ingredients of the catalyst in the form of the halide (e.g. as the chloride). This combined halogen may be either fluorine, chlorine, iodine, bromine, or mixtures thereof. Of these, fluorine and, particularly, chlorine are preferred for the purposes of the present invention. The halogen may be added to the carrier material in any suitable manner, either during preparation of the support or before or after the addition of the other components. For example, the halogen may be added, at any stage of the preparation of the carrier material or to the calcined carrier material, as an aqueous solution of a suitable, decomposable halogen-containing compound such as hydrogen fluoride, hydrogen chloride, hydrogen bromide, ammonium chloride, etc. The halogen component or a portion thereof, may be combined with the carrier material during the impregnation of the latter with the platinum group, cobalt, or zinc components; for example, through the utilization of a mixture of chloroplatinic acid and hydrogen chloride. In another situation, the alumina hydrosol which is typically utilized to form the preferred alumina carrier material may contain halogen and thus contribute at least a portion of the halogen component to the final composite. For the dehydrocyclization reaction, the halogen will be typically combined with the carrier material in an amount sufficient to result in a final composite that contains about 0.1 to about 3.5%, and preferably about 0.5 to about 1.5%, by weight of halogen, calculated on an elemental basis. It is to be understood that the specified level of halogen component in the instant catalyst can be achieved or maintained during use in the dehydrocyclization of hydrocarbons by continuously or periodically adding to the reaction zone a decomposable halogen-containing compound such as an organic chloride (e.g. ethylene dichloride, carbon tetrachloride, t-butyl chloride) in an amount of about 1 to 100 wt. ppm. of the hydrocarbon feed, and preferably, about 1 to 10 wt. ppm.

Regarding especially preferred amounts of the various metallic components of the subject catalyst, I have found it to be an excellent practice to specify the amounts of the cobalt component and the zinc component as a function of the amount of the platinum group component. On this basis, the amount of the cobalt component is ordinarily selected so that the atomic ratio of cobalt to platinum group metal contained in the composite is about 0.1:1 to about 66:1, with the preferred range being about 0.4:1 to about 18:1. Similarly, the amount of the zinc component is ordinarily selected to produce a composite containing an atomic ratio of zinc to platinum group metal of about 0.1:1 to about 10:1, with the preferred range being about 0.5:1 to about 5:1.

Another significant parameter for the instant catalyst is the "total metals content" which is defined to be the sum of the platinum group component, the cobalt component, and the zinc component, calculated on an elemental basis. Good results are ordinarily obtained with the subject catalyst when this parameter is fixed at a value of about 0.15 to about 4 wt. %, with best results ordinarily achieved at a metals loading of about 0.3 to about 3 wt. %.

Regardless of the details of how the components of the catalyst are combined with the porous carrier material, the final catalyst generally will be dried at a temperature of about 200° to about 600° F. for a period of at least about 2 to about 24 hours or more, and finally calcined or oxidized at a temperature of about 700° F. to about 1100° F. in an air to oxygen atmosphere for a period of about 0.5 to about 10 hours in order to convert substantially all of the metallic components to the corresponding oxide form. Because a halogen component is utilized in the catalyst, best results are generally obtained when the halogen content of the catalyst is adjusted during at least a portion of this oxidation step by including a halogen or a halogen-containing compound such as HCl or an HCl-producing substance in the air or oxygen atmosphere utilized. In particular, when the halogen component of the catalyst is chlorine, it is preferred to use a mole ratio of $H_2O$ to HCl to about 5:1 to about 100:1 during at least a portion of the oxidation step in order to adjust the final chlorine content of the catalyst to a range of about 0.1 to about 3.5 wt. %. Preferably, the duration of this halogenation step is about 1 to 5 hours.

The resultant oxidized catalytic composite is preferably subjected to a substantially water-free reduction step prior to its use in the dehydrocyclization of hydrocarbons. This step is designed to selectively reduce the platinum group component to the elemental metallic state, while preferably maintaining the zinc component in a positive oxidation state, and to insure a uniform and finely divided dispersion of the metallic components throughout the carrier material. Preferably, a substantially pure and dry hydrogen stream (i.e. less than 20 vol. ppm. $H_2O$) is used as the reducing agent in this step. The reducing agent is contacted with the oxidized catalyst at conditions including a reduction temperature of about 400° F. to about 1200° F. and a period of time of about 0.5 to 10 hours effective to reduce substantially all of the platinum group component to the elemental metallic state, while maintaining the zinc component in a positive oxidation state. Quite surprisingly, it has been found that if this reduction step is performed with a hydrocarbonfree hydrogen stream at the temperature indicated, and if the catalytically available cobalt component is properly distributed in the carrier material in the oxide form and in the specified particle size, a substantial amount of the catalytically available cobalt component may not be reduced in this step. However, once the catalyst sees a mixture of hydrogen and hydrocarbon (such as during the start-up and lining-out of the dehydrocyclization process using same), substantially all of the catalytically available cobalt component is quickly reduced at the specified reduction temperature range. This reduction treatment may be performed in situ as part of a start-up sequence if precautions are taken to predry the plant to a substantially water-free state and if a substantially water-free hydrogen stream is used.

The resulting selectively reduced catalytic composite is, in accordance with the basic concept of the present invention, preferably maintained in a sulfur-free state both during its preparation and thereafter during its use in the dehydrocyclization of hydrocarbons. As indicated previously, the beneficial interaction of the catalytically available cobalt component with the other ingredients of the present catalytic composite is contingent upon the maintenance of the cobalt moiety in a highly dispersed, readily reducible state in the carrier material. Sulfur in the form of sulfide adversely interferes with both the dispersion and reducibility of the catalytically available cobalt component and consequently it is a highly preferred practice to avoid presulfiding the selectively reduced acidic multimetallic catalyst resulting from the reduction step. Once the catalyst has been exposed to hydrocarbon for a sufficient period of time to lay down a protective layer of carbon or coke on the surface thereof, the sulfur sensitivity of the resulting carboncontaining composite changes rather markedly and the presence of small amounts of sulfur can be tolerated without permanently disabling the catalyst. The exposure of the freshly reduced catalyst to sulfur can seriously damage the cobalt component thereof and consequently, jeopardize the superior performance characteristics associated therewith. However, once a protective layer of carbon is established on the catalyst, the sulfur deactivation effect is less permanent and sulfur can be purged therefrom by exposure to a sulfur-free hydrogen stream at a temperature of about 800° to 1100° F.

According to the present invention, the dehydrocyclizable hydrocarbon is contacted with the instant acidic multimetallic catalyst in a dehydrocyclization zone maintained at dehydrocyclization conditions. This contacting may be accomplished by using the catalyst in a fixed bed system, a moving bed system, a fluidized bed system, or in a batch type operation; however, in view of the danger of attrition losses of the valuable catalyst and of well-known operational advantages, it is preferred to use either a fixed bed system or a dense-phase moving bed system such as is shown in U.S. Pat. No. 3,725,249. It is also contemplated that the contacting step can be performed in the presence of a physical mixture of particles of the catalyst of the present invention and particles of a conventional dual-function catalyst of the prior art. In a fixed bed system, the dehydrocyclizable hydrocarbon-containing charge stock is preheated by any suitable heating means to the desired reaction temperature and then passed into a dehydrocyclization zone containing a fixed bed of the acidic multimetallic catalyst. It is, of course, understood that the dehydrocyclization zone may be one or more separate reactors with suitable means therebetween to ensure that the desired conversion temperature is maintained at the entrance to each reactor. It is also important to note that the reactants may be contacted with the catalyst bed in either upward, downward, or radial flow fashion with the latter being preferred. In addition, the reactants may be in the liquid phase, a mixed liquid-vapor phase, or a vapor phase when they contact the catalyst, with best results obtained in the vapor phase. The dehydrocyclization system then preferably comprises a dehydrocyclization zone containing one or more fixed beds or dense-phase moving beds of the instant catalyst. In a multiple bed system, it is, of course, within the scope of the present invention to use the present catalyst in less than all of the beds with a conventional dual-function catalyst being used in the remainder of the beds. This dehydrocyclization zone may be one or more separate reactors with suitable heating means therebetween to compensate for the andothermic nature of the dehydrocyclization reaction that takes place in each catalyst bed.

Although hydrogen is the preferred diluent for use in the subject dehydrocyclization method, in some cases other art-recognized diluents may be advantageously utilized, either individually or in admixture with hydrogen, such as $C_1$ to $C_5$ paraffins such as methane, ethane, propane, butane and pentane; carbon dioxide, the like diluents, and mixtures thereof. Hydrogen is preferred because it serves the dual-function of not only lowering the partial pressure of the dehydrocyclizable hydrocarbon, but also of suppressing the formation of hydrogen-deficient, carbonaceous deposits (commonly called coke) on the catalytic composite. Ordinarily, hydrogen is utilized in amounts sufficient to insure a hydrogen to hydrocarbon mole ratio of about 0.1:1 to about 10:1, with best results obtained in the range of about 0.5:1 to about 5:1. The hydrogen stream charged to the dehydrocyclization zone will typically be recycle hydrogen obtained from the effluent stream from this zone after a suitable hydrogen separation step.

Since sulfur has a high affinity for cobalt at dehydrocyclization conditions, I have found that best results are achieved in a dehydrocyclization method using the instant acidic multimetallic catalytic composite when the catalyst is used in a substantially sulfur-free environment. The expression "substantially sulfur-free environment" is intended to mean that the total amount (expressed as equivalent elemental sulfur) of sulfur or sulfur-containing compounds, which are capable of producing a metallic sulfide at the reaction conditions used, entering the dehydrocyclization zone containing the instant catalyst from any source is continuously maintained at an amount equivalent to less than 10 wt. ppm. of the hydrocarbon charge stock, more preferably less than 5 wt. ppm., and most preferably less than 1 wt. ppm. Since in the ordinary operation of the subject dehydrocyclization method the influent hydrogen stream is autogenously produced, the prime source for any sulfur entering the dehydrocyclization zone is the hydrocarbon charge stock, maintaining the charge stock substantially free of sulfur is ordinarily sufficient to ensure that the environment containing the catalyst is maintained in the substantially sulfur-free state. More specifically, since hydrogen is a major product of the dehydrocyclization process, ordinarily the input diluent stream required for the process is obtained by recycling a portion of the hydrogen-rich stream recovered from the effluent withdrawn from the dehydrocyclization zone. In this typical situation, this recycle hydrogen stream will ordinarily be substantially free of sulfur if the charge stock is maintained free of sulfur. If autogenous hydrogen is not utilized as the diluent, then, of course, the concept of the present invention requires that the input diluent stream be maintained substantially sulfur-free; that is, less than 10 vol. ppm. of $H_2S$, preferably less than 5 vol. ppm., and most preferably less than 1 vol. ppm.

The only other possible sources of sulfur that could interfere with the performance of the instant catalyst are sulfur that is initially combined with the catalyst and/or with the plant hardware. As indicated hereinbefore, a highly preferred feature of the present acidic multimetallic catalyst is that it is maintained in a substantially sulfur-free state; therefore, sulfur released from the catalyst is not usually a problem in the present process. Hardware sulfur is ordinarily not present in a new plant; it only becomes a problem when the present process is to be implemented in a plant that has seen service with a sulfur-containing feed stream. In this latter case, the preferred practice of the present invention involves an initial pretreatment of the sulfur-containing plant in order to remove substantially all of the decomposable hardware sulfur therefrom. This can be easily accomplished by any of the techniques for stripping sulfur from hardware known to those in the art; for example, by the circulation of a substantially sulfur-free hydrogen stream through the internals of the plant at a relatively high temperature of about 800° to about 1200° F. until the $H_2S$ content of the effluent gas stream drops to a relatively low level—typically, less than 5 vol. ppm. and preferably less than 2 vol. ppm. In sum, the preferred sulfur-free feature of the present invention requires that the total amount of detrimental sulfur entering the dehydrocyclization zone containing the hereinbefore described acidic multimetallic catalyst must be continuously maintained at a substantially low level; specifically, the amount of sulfur must be held to a level equivalent to less than 10 wt. ppm., and preferably less than 1 wt. ppm., of the feed.

In the case where the sulfur content of the charge stock for the present process is greater than the amounts previously specified, it is, of course, necessary to treat the charge stock in order to remove the undesired sulfur contaminants therefrom. This is easily accomplished by using any one of the conventional catalytic pretreatment methods such as hydrorefining, hydrotreating, hydrodesulfurization, and the like to remove substantially all sulfurous, nitrogenous, and water-yielding contaminants from this feed stream. Ordinarily, this involves subjecting the sulfur-containing feed stream to contact with a suitable sulfur-resistant hydrorefining catalyst in the presence of hydrogen under conversion conditions selected to decompose sulfur contaminants contained therein and form hydrogen sulfide. The hydrorefining catalyst typically comprises one or more of the oxides or sulfides of the transition metals of Groups VI and VIII of the Periodic Table. A particularly preferred hydrorefining catalyst comprises a combination of a metallic component from the iron group metals of Group VIII and of a metallic component of the Group VI transition metals combined with a suitable porous refractory support. Particularly good results have been obtained when the iron group component is cobalt and/or nickel and the Group VI transition metal is molybdenum or tungsten. The preferred support for this type of catalyst is a refractory inorganic oxide of the type previously mentioned. For example, good results are obtained with a hydrorefining catalyst comprising cobalt oxide and molybdenum oxide supported on a carrier material comprising alumina and silica. The conditions utilized in this hydrorefining step are ordinarily selected from the following ranges: a temperature of about 600° to about 950° F., a pressure of about 500 to about 5000 psig., a liquid hourly space velocity of about 1 to about 20 hr.$^{-1}$, and a hydrogen circulation rate of about 500 to about 10,000 standard cubic feet of hydrogen per barrel of charge. After this hydrorefining step, the hydrogen sulfide, ammonia, and water liberated therein, are then easily removed from the resulting purified charge stock by conventional means such as a suitable stripping operation. Specific hydrorefining conditions are selected from the range given above as a function of the amounts and kinds of the sulfur contaminants in the feed stream in order to produce a substantially sulfur-free charge stock which is then charged to the process of the present invention.

It is also generally preferred to utilize the novel acidic multimetallic catalytic composite in a substantially water-free environment. Essential to the achievement of this condition in the dehydrocyclization zone is the control of the water level present in the charge stock and the diluent stream which is being charged to the zone. Best results are ordinarily obtained when the total amount of water entering the conversion zone from any source is held to a level less than 20 ppm. and preferably less than 5 ppm. expressed as weight of equivalent water in the charge stock. In general, this can be accomplished by careful control of the water present in the charge stock and in the diluent stream. The charge stock can be dried by using any suitable drying means known to the art, such as a conventional solid adsorbent having a high selectivity for water, for instance, sodium or calcium crystalline aluminosilicates, silica gel, activated alumina, molecular sieves, anhydrous calcium sulfate, high surface area sodium, and the like absorbents. Similarly, the water content of the charge stock may be adjusted by suitable stripping operations in a fractionation column or like device. And in some cases, a combination of adsorbent drying and distillation drying may be used advantageously to effect almost complete removal of water from the charge stock. In an especially preferred mode of operation, the charge stock is dried to a level corresponding to less than 5 wt. ppm. of $H_2O$ equivalent. In general, it is preferred to maintain the diluent stream entering the hydrocarbon conversion zone at a level of about 10 vol. ppm. of water or less and most preferably about 5 vol. ppm. or less. If the water level in the diluent stream is too high, drying of same can be conveniently accomplished by contacting this stream with a suitable desiccant such as those mentioned above.

The dehydrocyclization conditions used in the present method include a reactor pressure which is selected from the range of about 0 psig. to about 250 psig., with the preferred pressure being about 50 psig. to about 150 psig. In fact, it is a singular advantage of the present invention that it allows stable operation at lower pressure than have heretofore been successfully utilized in dehydrocyclization system with all platinum monometallic catalysts. In other words, the acidic multimetallic catalyst of the present invention allows the operation of a dehydrocyclization system to be conducted at lower pressure for about the same or better catalyst cycle life before regeneration as has been heretofore realized with conventional monometallic catalysts at higher pressure.

The temperature required for dehydrocyclization with the instant catalyst is markedly lower than that required for a similar operation using a high quality catalyst of the prior art. This significant and desirable feature of the present invention is a consequence of the extraordinary activity of the acidic multimetallic catalyst of the present invention for the dehydrocyclization reaction. Hence, the present invention requires a temperature in the range of from 800° F. to about 1100° F. and preferably about 850° F. to about 1000° F. As is well known to those skilled in the dehydrocyclization art, the initial selection of the temperature within this broad range is made primarily as a function of the desired conversion level of the dehydrocyclizable hydrocarbon considering the characteristics of the charge stock and of the catalyst. Ordinarily, the temperature then is thereafter slowly increased during the run to compensate for the inevitable deactivation that occurs to provide a relatively constant value for conversion. Therefore, it is a feature of the present invention that not only is the initial temperature requirement substantially lower, but also the rate at which the temperature is increased in order to maintain a constant conversion level is substantially lower for the catalyst of the present invention than for an equivalent operation with a high quality dehydrocyclization catalyst which is manufactured in exactly the same manner as the catalyst of the present invention except for the inclusion of the cobalt and zinc components. Moreover, for the catalyst of the present invention, the aromatic yield loss for a given temperature increase is substantially lower than for a high quality dehydrocyclization catalyst of the prior art.

The liquid hourly space velocity (LHSV) used in the instant dehydrocyclization method is selected from the range of about 0.1 to about 5 hr.$^{-1}$, with a value in the range of about 0.3 to about 2 hr.$^{-1}$ being preferred. In fact, it is a feature of the present invention that it allows operations to be conducted at higher LHSV than normally can be stably achieved in a dehydrocyclization process with a high quality dehydrocyclization catalyst of the prior art. This last feature is of immense economic significance because it allows a dehydrocyclization process to operate the same throughput level with less catalyst inventory or at greatly increased throughput level with the same catalyst inventory than that heretofore used with conventional dehydrocyclization catalysts at no sacrifice in catalyst life before regeneration.

The following working examples are given to illustrate further the preparation of the acidic multimetallic catalytic composite used in the present invention and the beneficial use thereof in the dehydrocyclization of hydrocarbons. It is understood that the examples are intended to be illustrative rather than restrictive.

These examples are all performed in a laboratory scale dehydrocyclization plant comprising a reactor, a hydrogen separating zone, heating means, cooling means, pumping means, compressing means, and the like conventional equipment. In this plant, a sulfur-free feed stream containing the dehydrocyclizable hydrocarbon is combined with a hydrogen recycle stream and the resultant mixture heated to the desired conversion temperature, which refers herein to the temperature maintained at the inlet to the reactor. The heated mixture is then passed into contact with the instant acidic multimetallic catalyst which is maintained in a sulfur-free and water-free environment and which is present as a fixed bed of catalyst particles in the reactor. The pressures reported herein are recorded at the outlet from the reactor. An effluent stream is withdrawn from the reactor, cooled, and passed into the hydrogen-separating zone wherein a hydrogen-containing gas phase separates from a hydrocarbon-rich liquid phase containing aromatic hydrocarbons, unconverted dehydrocyclizable hydrocarbons, and by-products of the dehydrocyclization reaction. A portion of the hydrogen-containing gas phase is recovered as excess recycle gas and the remaining portion is passed through a high surface area sodium scrubber and the resulting substantially water-free and sulfur-free hydrogen stream is recycled through suitable compressing means to the heating zone as described above. The hydrocarbon-rich liquid phase from the separating zone is withdrawn therefrom and subjected to analysis to determine conversion and selectivity for the desired aromatic hydrocarbon as will be indicated in the Examples. Conversion numbers of the dehydrocyclizable hydrocarbon reported herein are all calculated on the basis of disappearance of the dehydrocyclizable hydrocarbon and are expressed in weight percent. Similarly, selectivity numbers are reported on the basis of weight of desired aromatic hydrocarbon produced per 100 weight parts of dehydrocyclizable hydrocarbon charged.

All of the catalysts utilized in these examples are prepared according to the following general method with suitable modification in stoichiometry to achieve the compositions reported in each example. First, a sulfur-free alumina carrier material comprising 1/16 inch spheres having an apparent bulk density of about 0.5 g/cc is prepared by: forming an aluminum hydroxy chloride sol by dissolving substantially pure aluminum pellets in a hydrochloric acid solution, adding hexamethylenetetramine to the resulting alumina sol, gelling the resulting solution by dropping it into an oil bath to form spherical particles of an alumina hydrogel; aging, and washing the resulting particles with an ammoniacal solution and finally drying and calcining the aged and washed particles to form spherical particles of gamma-alumina containing about 0.3 wt. % combined chloride. Additional details as to this method of preparing this alumina carrier material are given in the teachings of U.S. Pat. No. 2,620,314.

The resulting sulfur-free gamma-alumina particles are then contacted at suitable impregnation conditions with a sulfur-free aqueous impregnation solution containing chloroplatinic acid, cobaltous chloride, zinc chloride and hydrogen chloride. The amounts of metallic reagents contained in this impregnation solution are carefully adjusted to yield a final multimetallic catalytic composite containing a uniform dispersion of the desired amounts of platinum, cobalt and zinc. The hydrochloric acid is utilized in an amount of about 5 wt. % of the alumina particles. In order to ensure a uniform dispersion of the metal moieties in the carrier material, the impregnation solution is maintained in contact with the carrier material particles for about ½ to about 3 hours at a temperature of about 70° F. with constant agitation. The impregnated spheres are then dried at a temperature of about 225° F. for about an hour and thereafter calcined or oxidized with a sulfur-free dry air stream at a temperature of about 930° F. and a GHSV of about 500 hr.$^{-1}$ for about ½ hour effective to convert substantially all of the metallic components to the corresponding oxide forms. In general, it is a good practice to thereafter treat the resulting oxidized particles with a sulfur-free air stream containing H$_2$O and HCl in a mole ratio of about 30:1 at a temperature of about 930° F. for an additional period of about 2 hours in order to adjust the combined chloride contained in the catalyst to a value of about 1 wt. %. The halogen-treated spheres are next subjected to a second oxidation step with a dry sulfur-free air stream at 930° F. and a GHSV of 500 hr.$^{-1}$ for an additional period of about ½ hour. The resulting oxidized and halogen-treated particles are thereafter subjected to a dry prereduction treatment designed, as pointed out hereinbefore, to reduce substantially all of the platinum component to the elemental metallic state, while maintaining substantially all of the zinc component in a positive oxidation state. This step involves contacting the catalyst particles with a substantially sulfur-free and hydrocarbon-free hydrogen stream containing less than 5 vol. ppm of H$_2$O at a temperature of 930° F., atmospheric pressure and a GHSV of about 400 hr.$^{-1}$ for a period of about 1 hour.

EXAMPLE I

The reactor is loaded with 100 cc of an acidic catalyst containing, on an elemental basis, 0.3 wt. % platinum, 1.0 wt. % cobalt, and 0.25 wt. % zinc, and about 1 wt. % chloride. This corresponds to an atomic ratio of cobalt to platinum of 11:1 and of zinc to platinum of 2.5:1. The feed stream utilized is commercial grade n-hexane. The feed stream is contacted with the catalyst at a temperature of 920° F., a pressure of 125 psig., a liquid hourly space velocity of 0.75 hr.$^{-1}$, and a hydrogen-containing recycle gas to hydrocarbon mole ratio of 4:1. The dehydrocyclization plant is lined-out at these conditions and a 20 hour test period commenced. The hydrocarbon product stream from the plant is continuously analyzed by GLC (gas liquid chromatography) and about a 90% conversion of n-hexane is observed with a selectivity for benzene of about 25%.

EXAMPLE II

The acidic catalyst contains, on an elemental basis, 0.375 wt. % platinum, 0.5 wt. % cobalt, 0.2 wt. % zinc and about 1 wt. % combined chloride. For this catalyst, the pertinent atomic ratios are: cobalt to platinum=4.4:1 and zinc to platinum=16:1. The feed stream is commercial grade normal heptane. The dehydrocyclization reactor is operated at a temperature of 900° F., a pressure of 125 psig., a liquid hourly space velocity of 0.75 hr.$^{-1}$, and a recycle gas to hydrocarbon mole ratio of 5:1. After a line-out period, a 20 hour test period is performed during which the average conversion of the n-heptane is maintained at about 95% with a selectivity for aromatics (a mixture of toluene and benzene of about 45%.

EXAMPLE III

The acidic catalyst is the same as utilized in Example II. The feed stream is normal octane. The conditions utilized are a temperature of 880° F., a pressure of 125 psig., a liquid hourly space velocity of 0.75 hr.$^{-1}$, and a recycle gas to hydrocarbon mole ratio of 4:1. After a line-out period, a 20 hour test shows an average conversion of about 100% and a selectivity for aromatics of about 50%.

EXAMPLE IV

The acidic catalyst contains, on an elemental basis, 0.2 wt. % platinum, 0.5 wt. % cobalt, 0.25 wt. % zinc and about 1 wt. % combined chloride. On an atomic basis, the ratio of cobalt to platinum is 8.3:1 and the ratio of zinc to platinum is 3.7:1. The feed stream is a 50/50 mixture of n-hexane and n-heptane. The conditions utilized are a temperature of 945° F., a pressure of 125 psig., a liquid hourly space velocity of 0.75 hr.$^{-1}$, and a recycle gas to hydrocarbon mode ratio of 5:1. After a line-out period, a 20 hour test is performed with a conversion of about 100% and a selectivity for aromatics of about 45%. The selectivity for benzene and toluene are about 20% and 25%, respectively.

It is intended to cover by the following claims, all changes and modifications of the above disclosure of the present invention which would be self-evident to a man of ordinary skill in the catalyst-formulation art or in the hydrocarbon dehydrocyclization art.

I claim as my invention:

1. A method for dehydrocyclizing a dehydrocyclizable hydrocarbon comprising contacting the hydrocarbon at hydrocarbon dehydrocyclization conditions with an acidic catalytic comprising a porous carrier material containing, on an elemental basis, about 0.01 to about 2 wt. % platinum group metal, about 0.05 to about 5 wt. % cobalt, about 0.01 to about 5 wt. % zinc and about 0.1 to about 3.5 wt. % halogen; wherein the platinum group metal, catalytically available cobalt and zinc components are uniformly dispersed throughout the porous carrier material; wherein substantially all of the platinum group component is present in the elemental metallic state; and wherein substantially all of the catalytically available cobalt component is present in the elemental metallic state or in a state which is reducible to the elemental metallic state under hydrocarbon dehydrocyclization conditions or in a mixture of these states.

2. A method as defined in claim 1 wherein the dehydrocyclizable hydrocarbon is admixed with hydrogen when it contacts the catalytic composite.

3. A method as defined in claim 1 wherein the platinum group component is platinum.

4. A method as defined in claim 1 wherein the platinum group component is palladium.

5. A method as defined in claim 1 wherein the platinum group component is iridium.

6. A method as defined in claim 1 wherein the platinum group component is rhodium.

7. A method as defined in claim 1 wherein the porous carrier material is a refractory inorganic oxide.

8. A method as defined in claim 7 wherein the refractory inorganic oxide is alumina.

9. A method as defined in claim 1 wherein the halogen is chlorine.

10. A method as defined in claim 1 wherein the dehydrocyclizable hydrocarbon is an aliphatic hydrocarbon containing 6 to 20 carbon atoms per molecule.

11. A method as defined in claim 10 wherein the aliphatic hydrocarbon is an olefin.

12. A method as defined in claim 10 wherein the aliphatic hydrocarbon is a paraffin.

13. A method as defined in claim 12 wherein the paraffin hydrocarbon is a paraffin containing 6 to 10 carbon atoms per molecule.

14. A method as defined in claim 12 wherein the paraffin is hexane.

15. A method as defined in claim 12 wherein the paraffin is heptane.

16. A method as defined in claim 12 wherein the paraffin is octane.

17. A method as defined in claim 12 wherein the paraffin is nonane.

18. A method as defined in claim 12 wherein the paraffin is a mixture of $C_6$ to $C_9$ paraffins.

19. A method as defined in claim 1 wherein the dehydrocyclizable hydrocarbon is contained in a naphtha fraction boiling in the range of about 140° F. to about 400° F.

20. A method as defined in claim 2 wherein the hydrocarbon dehydrocyclization conditions include a temperature of 800° to about 1100° F., a pressure of 0 to 250 psig., an LHSV of 0.1 to 5 hr.$^{-1}$, and a hydrogen to hydrocarbon mole ratio of about 0.1:1 to about 10:1.

21. A method as defined in claim 1 wherein the acidic catalytic composite contains, on an elemental basis, about 0.05 to about 1 wt. % platinum group metal, about 0.1 to about 2.5 wt. % cobalt and about 0.05 to about 1 wt. % zinc and about 0.5 to about 1.5 wt. % halogen.

22. A method as defined in claim 1 wherein the metals content of the catalytic composite is adjusted so that the atomic ratio of zinc to platinum group metal is about 0.1:1 to about 10:1 and the atomic ratio of cobalt to platinum group metal is about 0.1:1 to about 66:1.

23. A method as defined in claim 1 wherein the contacting is performed in a substantially water-free environment.

24. A method as defined in claim 1 wherein the contacting is performed in a substantially sulfur-free environment.

25. A method as defined in claim 1 wherein substantially all of the catalytically available cobalt component contained in the composite is present in the elemental metallic state after the method is started-up and lined-out at hydrocarbon dehydrocyclization conditions.

26. A method as defined in claim 1 wherein substantially all of the zinc component is present in the catalytic composite in a positive oxidation state.

27. A method as defined in claim 1 wherein the catalytic composite is in a sulfur-free state.

* * * * *